Figure 1:
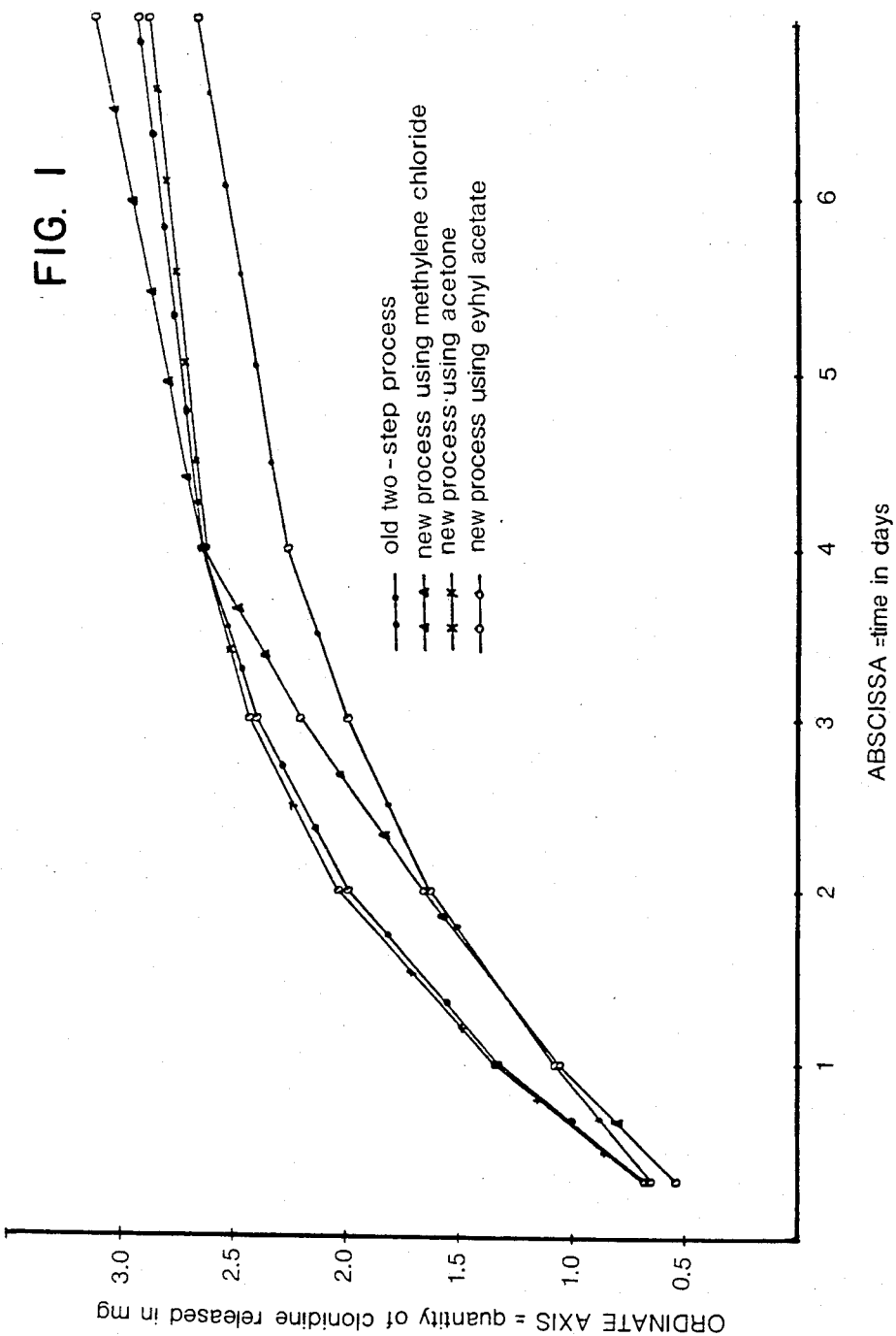

United States Patent [19]

Zierenberg

[11] Patent Number: 4,490,322
[45] Date of Patent: Dec. 25, 1984

[54] PROCESS FOR PRODUCING FILM

[75] Inventor: Bernd Zierenberg, Ingelheim am Rhein, Fed. Rep. of Germany

[73] Assignee: Boehringer Ingelheim K.G., Ingelheim am Rhein, Fed. Rep. of Germany

[21] Appl. No.: 463,589

[22] Filed: Feb. 3, 1983

[30] Foreign Application Priority Data

Feb. 10, 1982 [DE] Fed. Rep. of Germany ....... 3204551

[51] Int. Cl.$^3$ ...................... D01F 6/00; A61M 37/00; A61K 9/00
[52] U.S. Cl. .................................... 264/205; 264/216; 424/22; 424/28; 424/81; 604/896; 604/897
[58] Field of Search .................... 264/216, 210.6, 211; 424/28, 81, 22; 604/897, 896

[56] References Cited

U.S. PATENT DOCUMENTS 4,136,145  1/1979  Fuchs et al. ...................... 264/210.6

FOREIGN PATENT DOCUMENTS 1136045  11/1982  Canada .
2920500  11/1980  Fed. Rep. of Germany .

OTHER PUBLICATIONS

Ency. of Chem. Tech., vol. 8, "Emulsions", pp. 923–926.
Ency. of Chem. Tech., vol. 18, "Polymerization Processes", pp. 742–743.

Primary Examiner—Jay H. Woo
Assistant Examiner—Mike McGurk
Attorney, Agent, or Firm—Hammond & Littell, Weissenberger & Dippert

[57] ABSTRACT

A novel process for the preparation of a pharmaceutical preparation in the form of an polyacrylate film for long-term transdermal administration of systemic pharmaceuticals comprising forming a homogeneous solution of an effective amount of a systemically acting pharmaceutical and a freeze-dried latex of a polyacrylate copolymer of methyl and/or ethyl esters of acrylic acid and methacrylic acid formed by emulsion polymerization and having an average molecular weight of about 800,000 in at least one organic solvent, forming a thin layer of the said solution and drying the layer to form a polyacrylate film and the film product produced by the said process.

5 Claims, 4 Drawing Figures

PROCESS FOR PRODUCING FILM

STATE OF THE ART

It is known to embed pharmaceuticals in a polymer as can been seen for example from German Offenlegungsschrift No. 2,006,696 which describes a film generally consisting of copolymers of acrylates and methacrylates and containing active substances such as -contraceptives in a homogeneous mixture. Films of this kind are used in conjunction with a plaster or adhesive bandage so that the active substances are released transdermally. U.S. Pat. No. 4,076,798 describes a pharmaceutical preparation for the continuous, regulated administration of a predetermined quantity of active substance wherein the support or carrier for the pharmaceutical preparation is a biodegradable, hydrolyzable polyester resin of diglycolic acid.

Finally, German Offenlegunsschrift No. 2,920,500 discloses a pharmaceutical composition in the form of polyacrylate film consisting of a copolymer obtained from alkyl esters of acrylic acid and methacrylic acid which is compatible with the skin and which swells in water, the active substance being embedded therein in amorphous form, the characterising feature of this film being that it has a concentration gradient of active substance with the concentration of active substance in the polymer film increasing with its distance from the release surface. This pharmaceutical preparation is produced by first dissolving any excipients or adjuvants in the aqueous polyacrylate dispersion and then dissolving the pharmaceutical substances therein in the required quantity, if these pharmaceutical substances are readily water-soluble. The dispersion is then poured out onto a bounded planar surface and left to dry to a film, possibly at elevated temperatures. Then the active substances are applied to the polyacrylate film in the form of an organic solution and the solvent is evaporated off. If required, to vary the concentration profile of active substance over the cross section of the film, more of the dispersion may be applied once or several times to one or both sides of the prepared film and active substance may be added thereto, and after suitable packaging, this film constitutes the finished pharmaceutical preparation. Among the particularly important factors which influence the speed of release are the conditions under which the polyacrylate film is charged with active substance.

Recent tests have shown that this two-step process in German Offenlegungsschrift No. 2,920,500 does indeed initially produce a polyacrylate film with a concentration gradient of active substance but that, when the film is stored for any length of time before being used, the concentration profile evens out as a result of internal diffusion processes. After lengthy storage, the films have a homogeneous distribution of the pharmaceutical substance in the polyacrylate film.

Moreover, in continuous production, the second stage of the treatment, namely the charging of the polyacrylate film with a solution of the active substance, presents some technical problems since the film softens and becomes distorted as a result of coming into contact with the organic solvent. As a result, the pieces stamped out from a film produced in this way have considerable standard deviations in the rate of release of the active substance.

OBJECTS OF THE INVENTION

It is an object of the invention to provide an improved and rapid, continuous process for the preparation of films containing a systemic pharmaceutical for prolonged transdermal administration of the pharmaceutical.

It is another object of the invention to provide an improved film of a systemic pharmaceutical for prolonged transdermal administration thereof.

These and other objects and advantages of the invention will become obvious from the following detailed description.

THE INVENTION

The novel process of the invention for the preparation of a pharmaceutical preparation in the form of an polyacrylate film for long-term transdermal administration of systemic pharmaceuticals comprises forming a homogeneous solution of an effective amount of a systemically acting pharmaceutical and a freeze-dried latex of a polyacrylate copolymer of methyl and/or ethyl esters of acrylic acid and methacrylic acid formed by emulsion polymerization having an average molecular weight of about 800,000 in at least one organic solvent, forming a thin layer of the said solution and drying the layer to form a polyacrylate film containing the systemic pharmaceutical. The process is rapid and continuous and is reduced to a single step.

It has been found, in particular, that when producing a transdermal release system based on a polyacrylate film, it is particularly important to use an acrylate material which has been polymerized in a particular way. The acrylate copolymer must be produced by emulsion polymerization and it should preferably have an average molecular weight of about 800,000 and a particle size of approximately 140 nm. Polyacrylates produced by other methods, e.g. by solution polymerization or block polymerization, are unsuitable for the purposes of the invention. The recovery of the solids from the emulsion can best be effected by freeze drying whereby the particles of polymer retain their shape and size.

Other methods of obtaining the polymer from the latex have proved less practicable. A suitable starting material is the commercially available product known as Eudragit E 30 D or Plex 47 91 D made by Messrs Röhm of Darmstadt. However, it is also possible to use other polyacrylate latices which correspond to the above products in their molecular weight and particle size.

The freeze-dried latex is taken up in an organic solvent or mixture of solvents capable of dissolving both the pharmaceutical substance and also the polyacrylate. Suitable solvents include lower aliphatic alcohols, ethers, ketones, esters, hydrocarbons or halohydrocarbons, particularly those having a boiling point below 100° C. and are readily capable of being evaporated. Mixtures of solvents may be used. By a suitable choice of solvent or mixture of solvents, it is possible to alter the viscosities of the starting solution.

Normally, the solutions will have a viscosity of 200 to 1000 cPs measured at 20° C. and the concentration of the copolymer in the solution may vary from 2 to 15% by weight and the concentration of the systemic pharmaceutical can vary between 0.01 to 3% by weight. Normally, the film will contain a weight ratio of copolymer to pharmaceutical of 0.5 to 20, preferably 5 to 12.

The characteristics of release of the pharmaceutical substances from the polymer matrix in film form can be controlled, particularly if the pharmaceutical substances in question are acidic or basic. Thus the speed of release of acidic or basic active substances can be varied by using polyacrylates containing acid or basic groups such as carboxylic or amino or dialkylamino groups. Generally, it is preferred to use copolymers or mixtures of copolymers containing 0 to 10 mole % of acid or basic monomer units.

The films should normally have a thickness of about 50 to 200 μm. The temperature at which the solution is dried to a film is normally within the range from room temperature to at most the reflux temperature of the solvent or mixture of solvents used; normally, owing to the instability of many pharmaceutical substances and the risk of the formation of bubbles in the film, the drying is normally carried out at the lowest possible temperature. The production of the film may be continuous or discontinuous process.

The films obtained are cut up or stamped out into suitable pieces and packaged in the usual way to produce forms for transdermal administration, for example by applying a support and/or covering layer to one side of the film containing the active substance and applying an adhesive layer with a removable protective coating to the other side.

The film preparations produced by the process of the invention were compared with films corresponding to German Auslegeschrift No. 2,920,500 to study their release characteristics and it was found that there were no significant differences between the two types of film.

In the following examples, there are described several preferred embodiments to illustrate the invention. However, it is to be understood that the invention is not intended to be limited to the specific embodiments.

In the Examples, Eudragit E 30 D made by Messrs. Röhm of Darmstadt was used as the polyacrylate.

EXAMPLE 1

Active substance: Clonidine

A. 8 g of freeze-dried polyacrylate, 1 g of clonidine and 91 g of acetone were placed in a vessel and stirred for about 12 hours with a magnetic stirrer until a homogeneous, relatively viscous solution was obtained and this solution was then poured into casting moulds in a quantity of 190 mg/cm$^2$. After standing about 6 hours at ambient temperature, the acetone solvent had evaporated off and a smooth film was obtained, containing 8.4 mg of polyacrylate and 1 mg of clonidine per cm$^2$.

B. The starting solution had the following composition of 6 g of polyacrylate, 0.53 g of clonidine and 93.5 g of ethyl acetate. When applied to the casting moulds in a quantity of 390 mg/cm$^2$, a film containing 1 mg of clonidine and 11.6 mg of polyacrylate per cm$^2$ was obtained.

C. The composition of the starting solution was 3 g of polyacrylate, 0.37 g of clonidine and 96.6 g of methylene chloride and when applied to the casting moulds in a quantity of 650 mg/cm$^2$, a film containing 1 mg of clonidine and 9.64 mg of polyacrylate per cm$^2$ was obtained after drying.

All three solvents produced clear, transparent films in which the pharmaceutical substance was present in a molecular dispersion.

The quantity of clonidine released in vitro as a function of time is shown in FIG. 1; as a comparison, the release curve for a film produced by the two-step method in German Offenlegungsschrift No. 2,920,500 (charged with the solvent methanol) is also shown. The films produced by the new method are distinguished from the old films by their much smaller standard deviation in the rate of release between the individual stamped pieces. The variation between individuals is 1%, whereas it is about 6% for the prior art films. This means that the films produced by the new process have greater homogeneity.

EXAMPLE 2

Active substance: dihydroergotamine methanesulfonate

Figure 2:
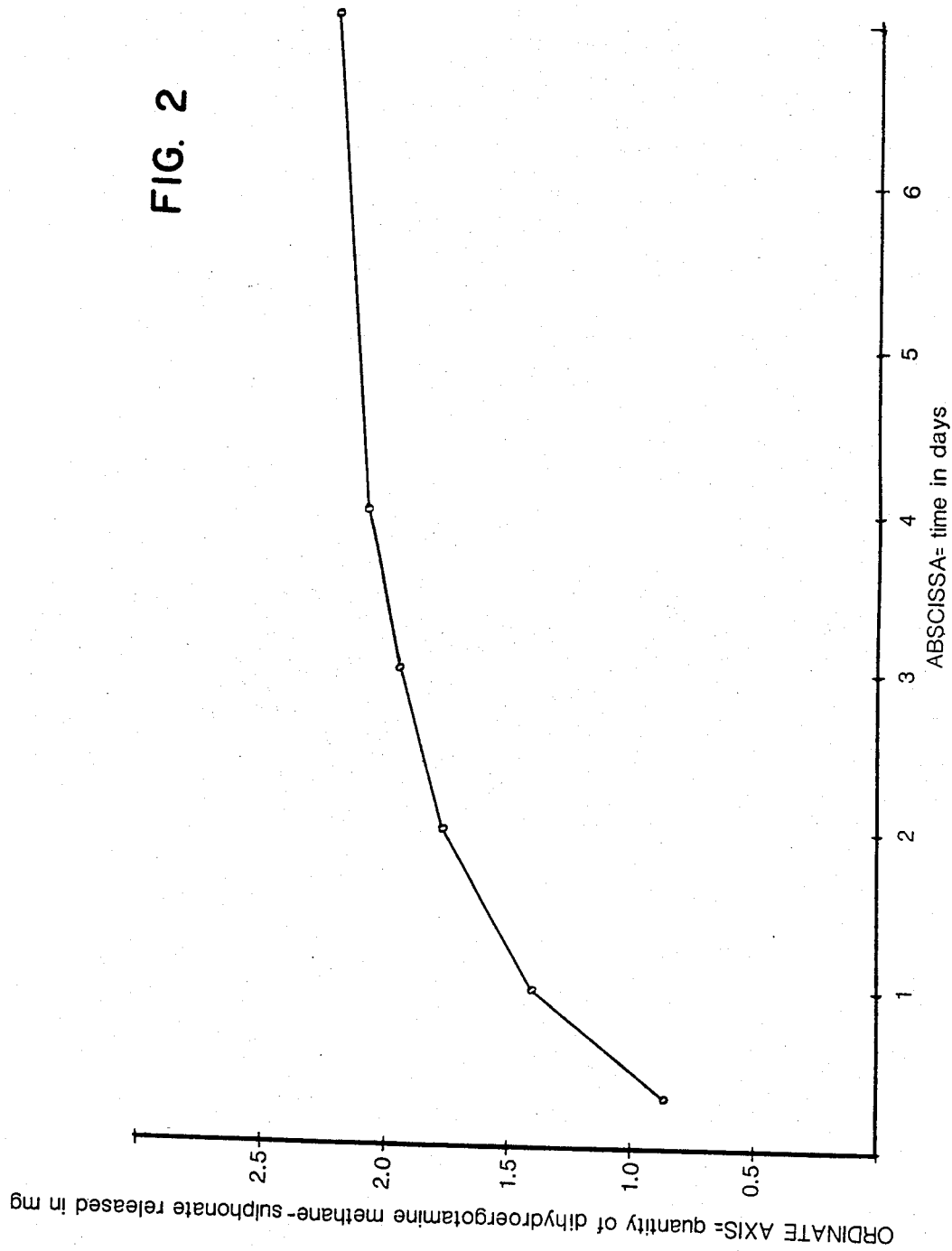

The composition of the starting solution was 8.75 g of polyacrylate, 1.375 g of dihydroergotamine methanesulfonate and 90.875 g of methanol and when a quantity of 244 mg/cm$^2$ was applied to the casting moulds, a film containing 16.6 mg of polyacrylate and 0.96 g of dihydroergotamine methanesulfonate per cm$^2$ was obtained after drying. The quantity of active substance released in vitro as a function of time is shown in FIG. 2.

EXAMPLE 3

Active substance: scopolamine

Figure 3:
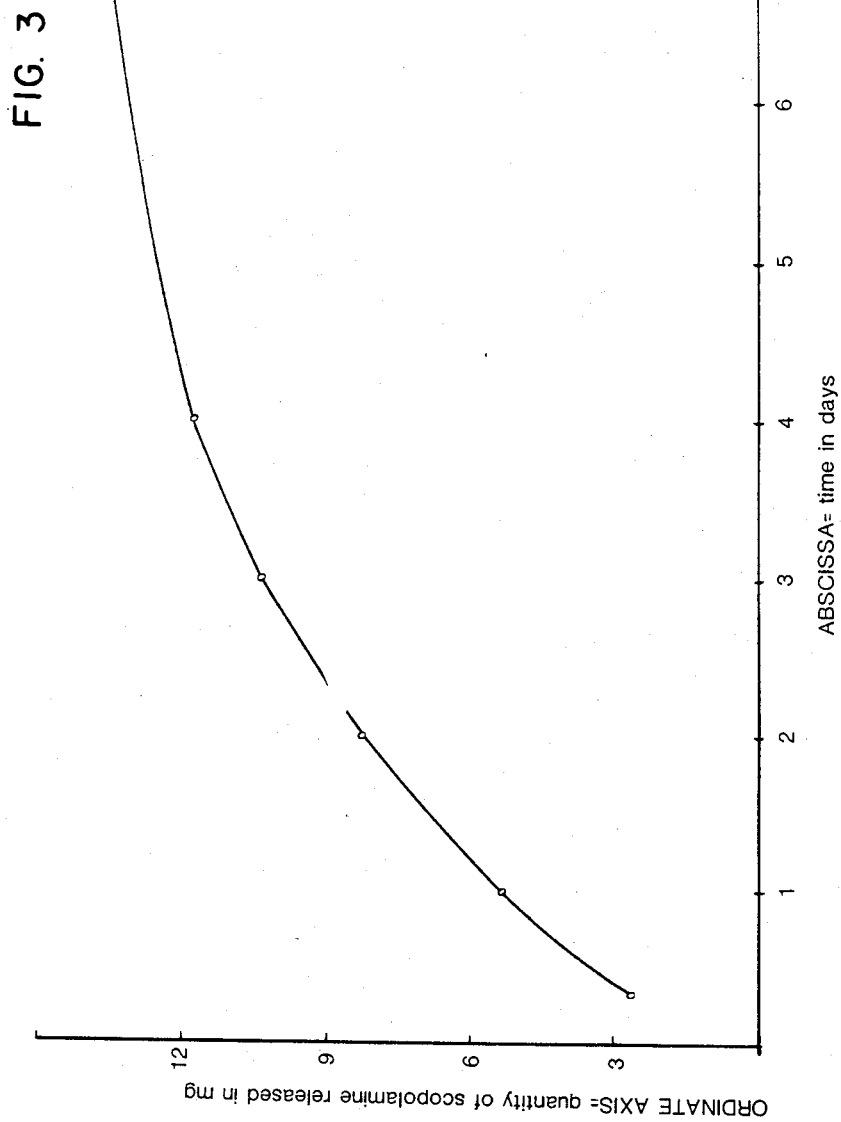

The composition of the starting solution was 12.0 g of polyacrylate, 3 g of scopolamine base and 85 g of acetone. When a quantity of 667 mg/cm$^2$ was applied to the casting moulds, a film containing 22.3 mg of polyacrylate and 5.6 mg of scopolamine per cm$^2$ was obtained after drying. The curve for release in vitro is shown in FIG. 3.

EXAMPLE 4

Active substance: clonidine

In this example, a mixture of polyacrylates was used in which, some of the product E 30 D was replaced by a copolymer consisting of 50 mol % of acrylic acid and 50% of methyl acrylate, marketed under the name L 100 by Messrs. Röhm of Darmstadt.

A. The starting solution had the following composition: 6.3 g of polyacrylate E 30 D, 0.7 g of polyacrylate L 100, 0.875 g of clonidine, 46 g of acetone and 46 g of ethanol and when it was applied to the casting moulds in a quantity of 210 mg/cm$^2$, a film containing 1 mg of clonidine and 7.85 mg of polyacrylate per cm$^2$ was obtained after drying.

B. The composition of the starting solution was 5.6 g of polyacrylate E 30 D, 1.4 g of polyacrylate L 100, 0.875 g of clonidine, 46 g of acetone and 46 g of ethanol and when a quantity of 210 mg of casting solution per cm$^2$ was applied to the casting moulds, a film containing 1 mg of clonidines and 7.85 mg of polyacrylate per cm$^2$ was obtained after drying.

Figure 4:
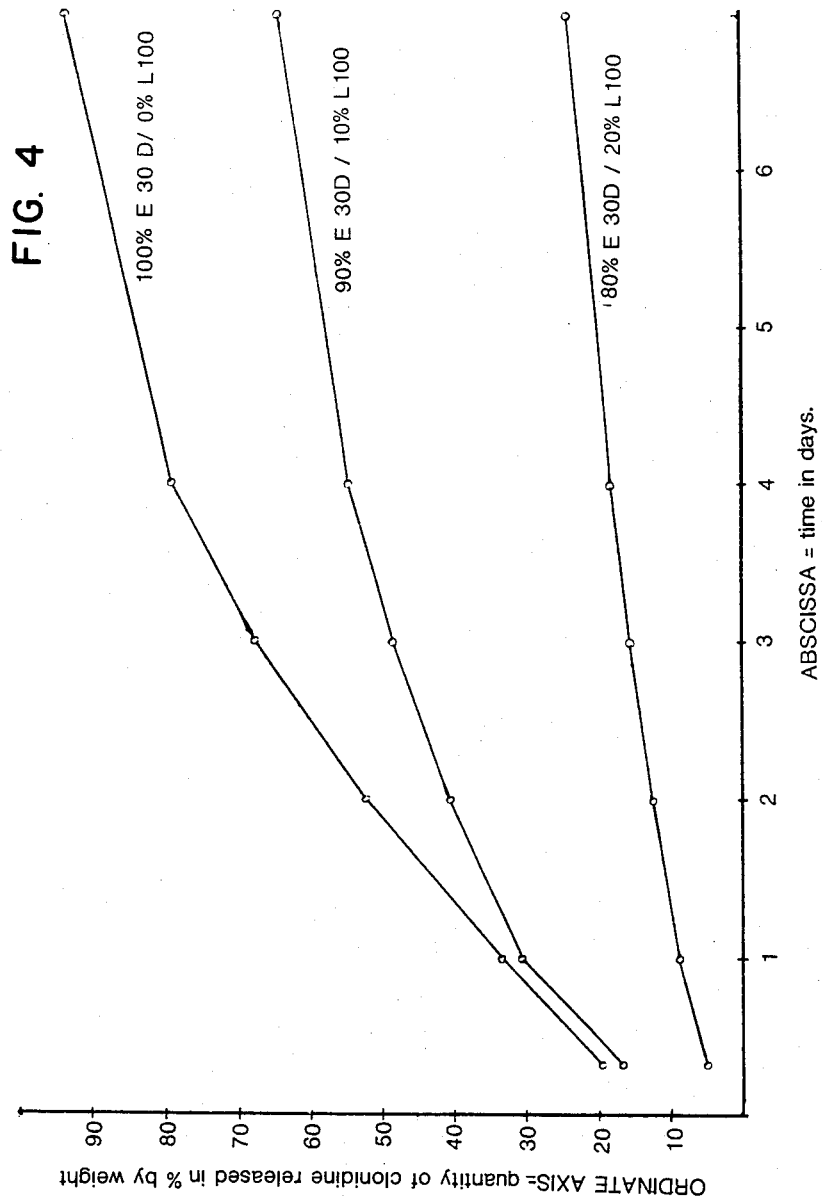

FIG. 4 shows the release curves of Examples 1A, 4A, and 4B by way of a comparison and it can be seen that the diffusion is slowed down considerably by salt formation of clonidine with the polymeric acrylic acid embedded in the polyacrylate E 30 D. As an estimate, it can be said that the speed of release is reduced to about one fifth when there is twice the equimolar quantity of carboxyl groups in the polymer based on the quantity of active substance base.

Various modification of the products and process of the invention may be made without departing from the spirit or scope thereof and it is to be understood that the invention is intended to be limited only as define in the appended claims.

What I claim is:

1. A process for the preparation of a pharmaceutical composition in the form of a polyacrylate film for long-term transdermal administration of systemic pharmaceuticals, which comprises forming a homogeneous solution of an effective amount of a systemically acting pharmaceutical and a freeze-dried latex of a polyacrylate copolymer having a polymer unit of the formula

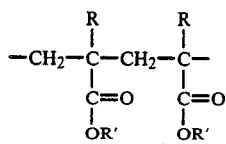

where
R is H or $CH_3$ and
R' is $CH_3$ or $C_2H_5$
formed by emulsion polymerization and having an average molecular weight of about 800,000 in an organic solvent, forming a thin layer of the said solution, and drying the layer to form a polyacrylate film.

2. The process of claim 1 wherein the film is prepared continuously.

3. The process of claim 1 wherein the film is prepared discontinuously.

4. The process of claim 1 wherein the drying of the film is effected at a temperature from room temperature to the boiling point of the solvent.

5. The process of claim 1 wherein the polyacrylate contains polyacrylate containing acidic or basic groups.